US011980447B2

(12) United States Patent
Morris et al.

(10) Patent No.: US 11,980,447 B2
(45) Date of Patent: May 14, 2024

(54) ESOPHAGEAL DEFLECTION DEVICE

(71) Applicant: The Regents of the University of California, Oakland, CA (US)

(72) Inventors: Karcher Morris, La Jolla, CA (US); Anay Mahesh Pandit, La Jolla, CA (US); Thomas Savides, La Jolla, CA (US); Young Seo, La Jolla, CA (US); Frank Talke, La Jolla, CA (US); Youyi Fu, La Jolla, CA (US); Greg Feld, La Jolla, CA (US); Scott Garner, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 248 days.

(21) Appl. No.: 16/488,453

(22) PCT Filed: Mar. 8, 2018

(86) PCT No.: PCT/US2018/021557
§ 371 (c)(1),
(2) Date: Aug. 23, 2019

(87) PCT Pub. No.: WO2018/165435
PCT Pub. Date: Sep. 13, 2018

(65) Prior Publication Data
US 2020/0029822 A1 Jan. 30, 2020

Related U.S. Application Data

(60) Provisional application No. 62/468,697, filed on Mar. 8, 2017.

(51) Int. Cl.
*A61B 1/005* (2006.01)
*A61B 1/12* (2006.01)
(Continued)

(52) U.S. Cl.
CPC ............ *A61B 5/015* (2013.01); *A61B 1/0055* (2013.01); *A61B 1/128* (2013.01); *A61B 5/01* (2013.01);
(Continued)

(58) Field of Classification Search
CPC ....... A61B 5/015; A61B 1/0055; A61B 1/128; A61B 5/01; A61B 5/6855; A61B 5/687;
(Continued)

(56) References Cited

U.S. PATENT DOCUMENTS 5,620,479 A * 4/1997 Diederich .............. A61B 18/18
601/3
6,259,938 B1 7/2001 Zarychta et al.
(Continued)

FOREIGN PATENT DOCUMENTS

EP 2898815 A1 7/2015
WO 2009117523 A2 9/2009
WO 2011143486 A1 11/2011

OTHER PUBLICATIONS

Chugh et al., "Mechanical displacement of the esophagus in patients undergoing left atrial ablation of atrial fibrillation", Heart Rhythm, Mar. 2009, pp. 319-322, vol. 6, No. 3, Heart Rhythm Society.
(Continued)

*Primary Examiner* — Daniel L Cerioni
(74) *Attorney, Agent, or Firm* — Greer, Burns & Crain, Ltd.; Steven P. Fallon

(57) ABSTRACT

An esophageal deflection device includes an elongate outer tube that has a natural curved deflection at a position that corresponds to a targeted esophagus region for deflection. The outer diameter of the outer tube is substantially matched to an inner diameter of the esophagus to closely contact the esophagus wall, or is at least half of the inner diameter, or is smaller and includes suction ports for drawing the esopha-
(Continued)

gus wall inward. An insertion rod or tube includes a portion that is stiffer than the curved deflection, and slides into the elongate outer tube to straighten the tube and can serve to guide the deflection device into an esophagus. Subsequent withdrawal of the insertion tube or rod will allow the curved deflection to return to its natural shape and deflect the targeted region of the esophagus.

14 Claims, 11 Drawing Sheets

(51) Int. Cl.
    *A61B 5/00*     (2006.01)
    *A61B 5/01*     (2006.01)
    *A61M 25/00*     (2006.01)
    *A61M 25/01*     (2006.01)

(52) U.S. Cl.
    CPC ............ *A61B 5/6855* (2013.01); *A61B 5/687* (2013.01); *A61B 5/6879* (2013.01); *A61M 25/0054* (2013.01); *A61M 25/0108* (2013.01); *A61M 25/0136* (2013.01)

(58) Field of Classification Search
    CPC ............ A61B 5/6879; A61M 25/0054; A61M 25/0108; A61M 25/0136
    See application file for complete search history.

(56) References Cited

U.S. PATENT DOCUMENTS

| | | |
|---|---|---|
| 7,621,908 B2 | 11/2009 | Miller |
| 8,273,016 B2 | 9/2012 | O'Sullivan |
| 8,529,443 B2 | 9/2013 | Maloney |
| 9,393,071 B1 | 7/2016 | Boveja et al. |
| 2003/0032865 A1* | 2/2003 | Estes .................. A61B 17/1757 600/226 |
| 2007/0093858 A1* | 4/2007 | Gambale ............ A61B 17/0487 606/142 |
| 2008/0033415 A1 | 2/2008 | Rieker et al. |
| 2011/0034936 A1 | 2/2011 | Maloney |
| 2011/0282338 A1 | 11/2011 | Fojtik |
| 2012/0010524 A1 | 1/2012 | Fojtik et al. |
| 2013/0211282 A1 | 8/2013 | Bunch et al. |
| 2015/0289753 A1 | 10/2015 | Kimura |

OTHER PUBLICATIONS

Shuraih et al., "Strategies to Prevent Esophageal Injury During Catheter Ablation of Atrial Fibrillation", The Journal of Innovations in Cardiac Rhythm Management, Apr. 2012, pp. 719-726, vol. 3, Innovations in Cardiac Rhythm Management.
International Search Report from the corresponding International Patent Application No. PCT/US2018/021557, dated May 25, 2018.
European Search Report from the corresponding European Patent Application No. 18764426, dated Nov. 13, 2020.
Office Action from the corresponding Japanese Patent Application No. 2019-548619, dated Dec. 1, 2020.

* cited by examiner

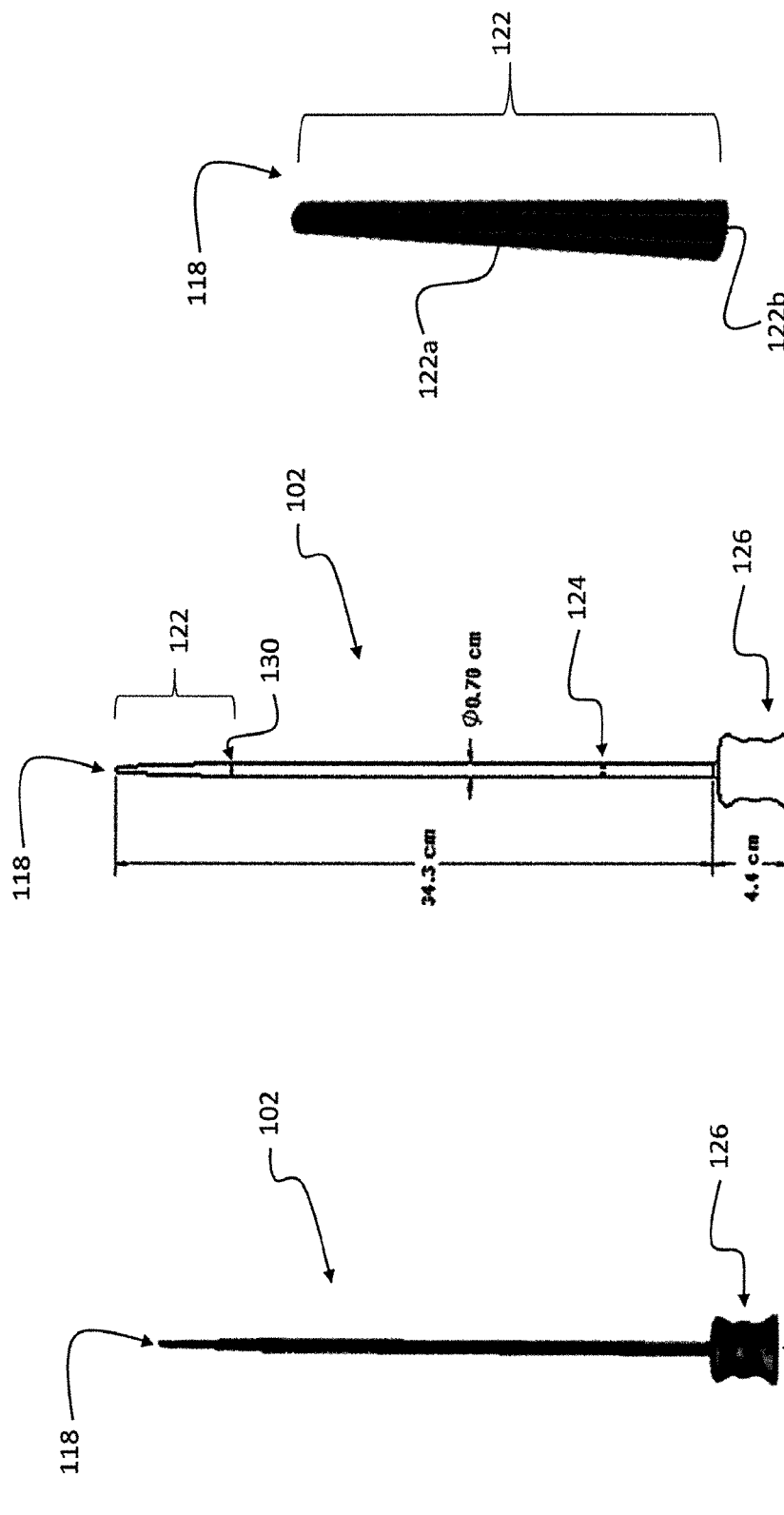

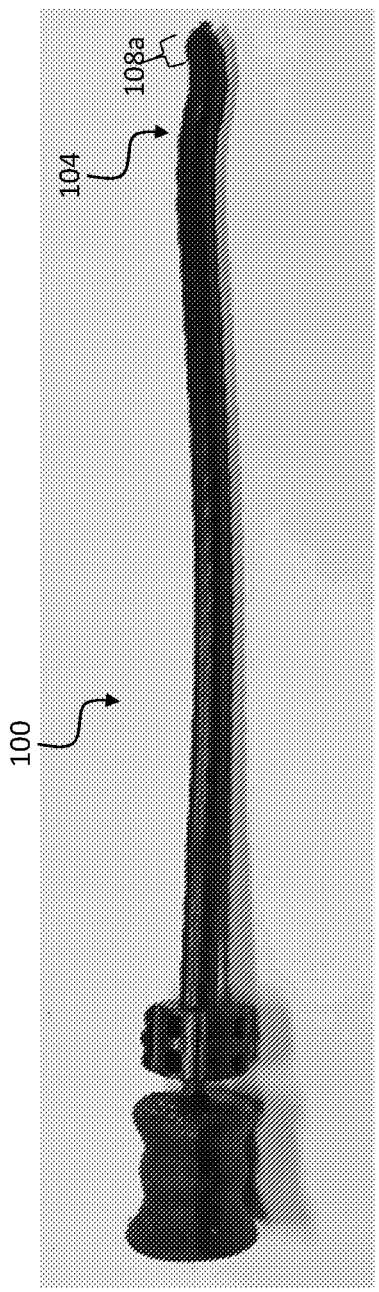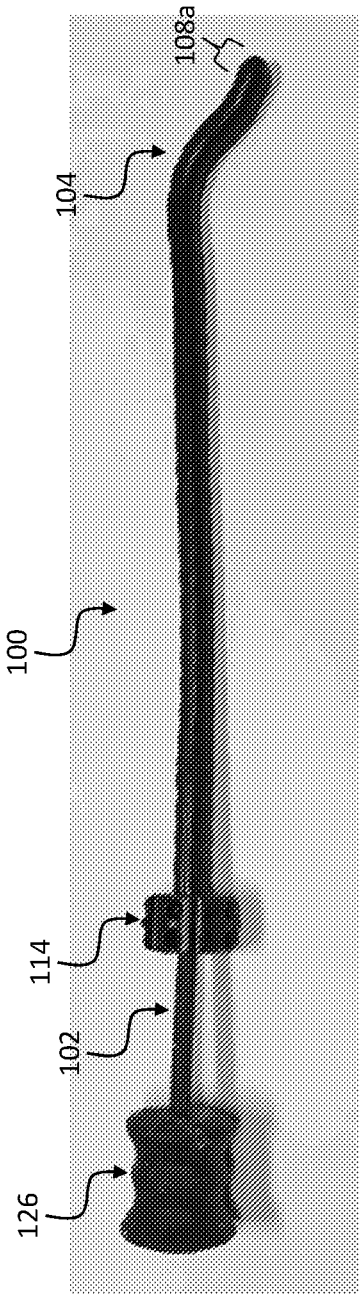
FIG. 2A
FIG. 2B

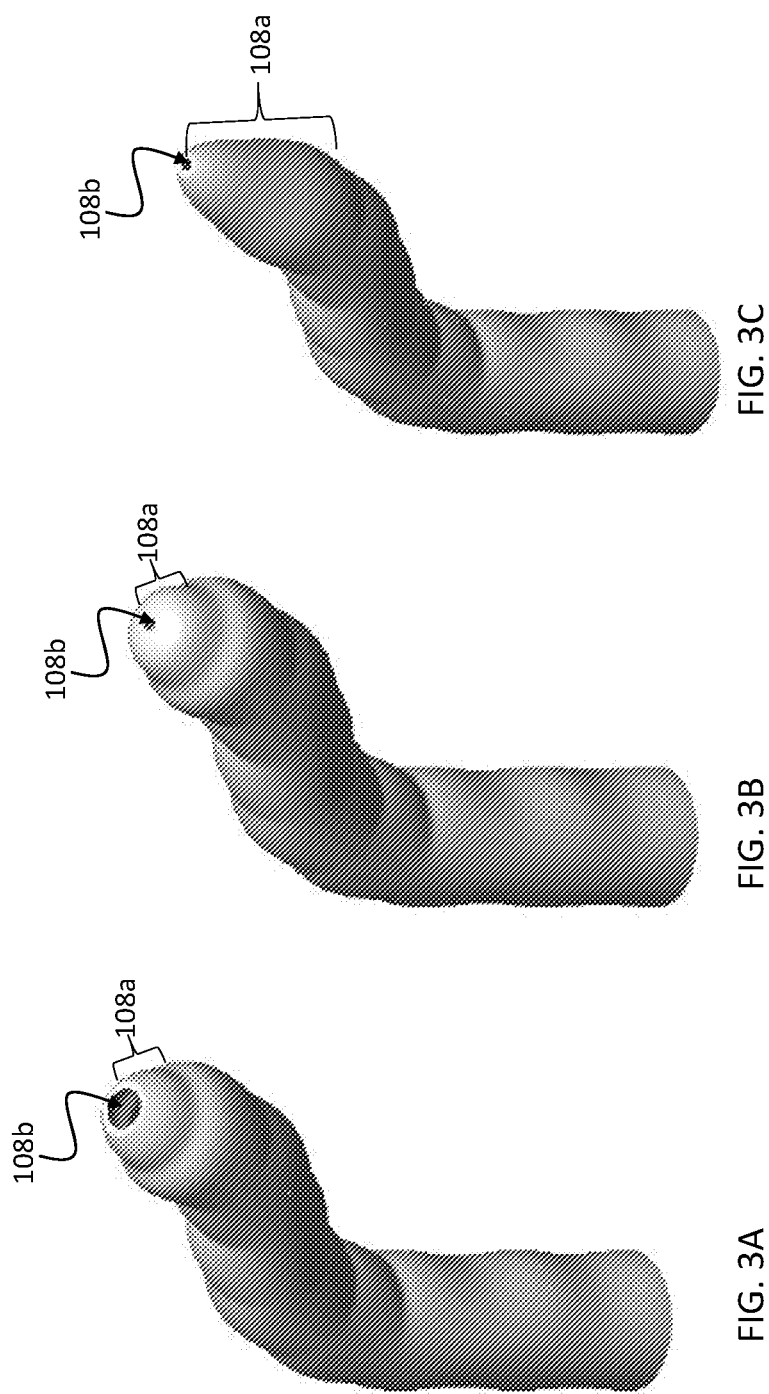

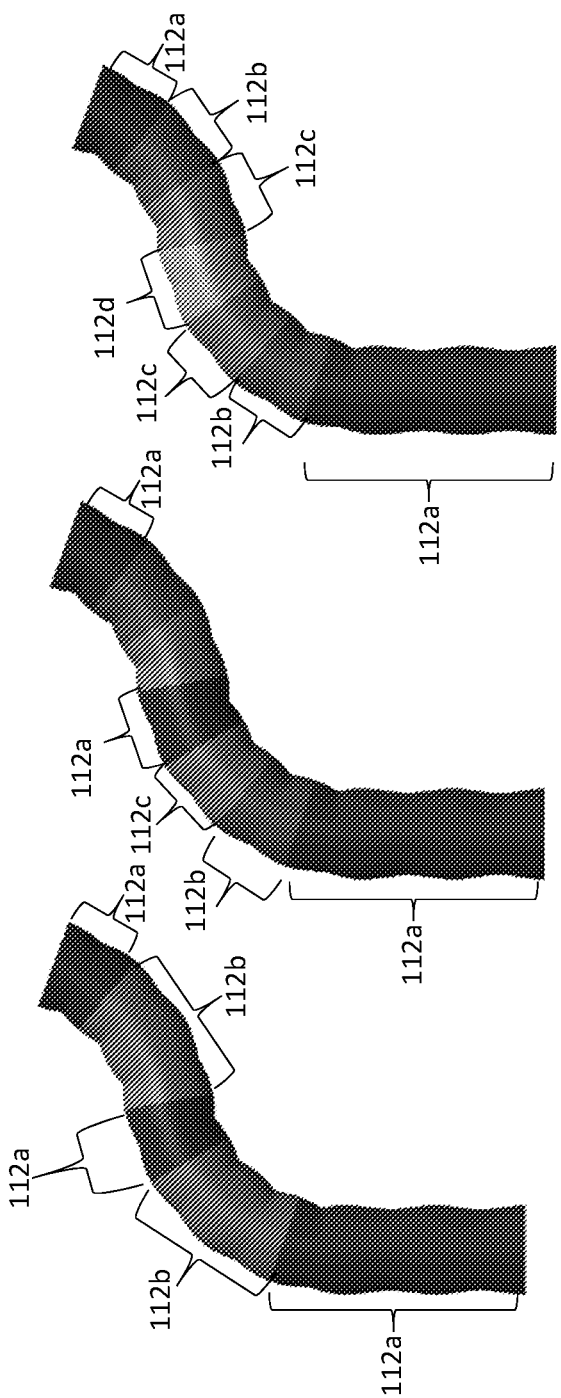

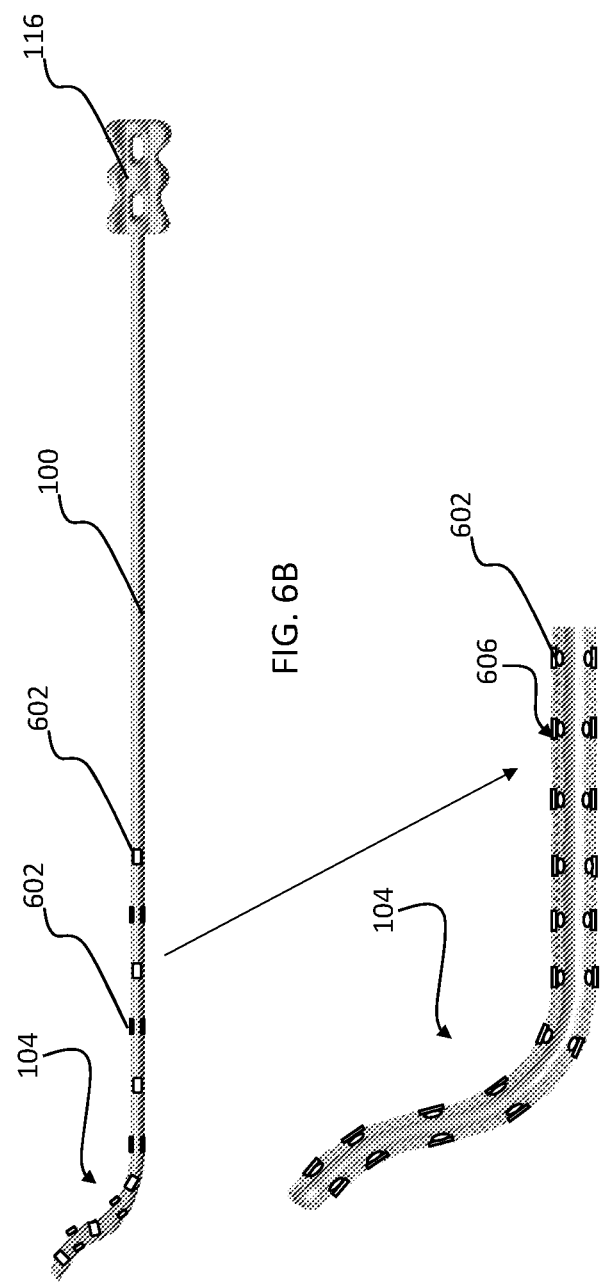

ESOPHAGEAL DEFLECTION DEVICE

PRIORITY CLAIM AND REFERENCE TO RELATED APPLICATION

The application claims priority under 35 U.S.C. § 119 and all applicable statutes and treaties from prior U.S. provisional application Ser. No. 62/468,697, which was filed Mar. 8, 2017.

FIELD

A field of the invention is medical devices, and particularly surgical devices. The invention provides a device that can safely deflect the esophagus during procedures. Example procedures that would benefit from the use of the device of the invention include thermal ablation of the left atrium.

BACKGROUND

Esophageal deflection is a critical step to certain surgical procedures. Catheter ablation is a procedure used to treat patients with refractory paroxysmal and persistent atrial fibrillation. Ablation changes electrical current paths in heart tissue by locally targeting cells that are supporting a problematic current path. In the example of ablation applied to treat arterial fibrillation, a common strategy is the creating of lesions at particular target locations, such as the left atrial roof, mitral isthmus, or posterior wall. One of the highest risks during the ablation procedure is damage to the esophagus. The esophagus is often very close to or in contact with the left atrium. Damage inflicted on esophageal cells during the ablation can lead to death.

A factor leading to damage and death has been the sensitivity of esophageal tissue to RF energy and/or heat, both of which can damage esophageal tissue directly and/or esophageal arteries. See, Shuraih et al, "Strategies to Prevent Esophageal Injury During Catheter Ablation of Atrial Fibrillation," The Journal of Innovations in Cardiac Rhythm Management, 3 (2012), 719-726. Techniques employed previously include gastric acid suppression, esophageal temperature monitoring, thermal insulation of the esophagus, energy limitation, esophagus cooling, and mechanical deflection of the esophagus. Shuraih et al, supra. Shuraih et al. note that the prior techniques requirement improvement to reduce the incidence of the often fatal complication of esophageal damage during ablation.

A mechanical deflection technique proposed in the past is the deflection of the esophagus with an endoscope. Chugh et al., Mechanical Displacement of the Esophagus in Patients Undergoing Left Atrial Ablation of Atrial Fibrillation," Heart Rhythm 2009 March; 6(3): 319-22. An endoscopist deflected the esophagus immediately prior to ablation and then removed the endoscope. The esophagus remained deflected in a minority of the patients after the esophagus was removed. The endo scope must be removed during the ablation procedure to provide safety during the ablation energy transfer. This mechanical deflection procedure therefore does not ensure displacement of the esophagus during ablation. As noted in the publication: "Why the esophagus could not be displaced in all patients is not clear. Possible reasons include decreased laxity of attachments to surrounding structures, increased compliance of the esophageal wall resulting in distension of the esophageal lumen rather than translocation of body of the esophagus, and variations in technique. Another possibility is decreased compliance of the surrounding tissues, such as the PVs and/or their antra." In addition, initial displacements were often lost, in "most patients in this study, the esophagus assumed its original position after the endo scope was removed, as might be expected given the elastic nature of the esophageal wall and its connective tissues. Esophageal rebound to its original position might hinder the safe delivery of radiofrequency energy. A strategy for overcoming this limitation is delivery of radiofrequency current while the esophagus is being actively displaced with the endoscope. However, there is a theoretical concern of shunting radiofrequency energy to the endoscope, which could result in thermal injury to the esophagus."

O'Sullivan U.S. Pat. No. 8,273,016 describes an esophagus isolation catheter. The catheter has deflectable intermediate section and a straight tip or a deflectable tip section mounted at the distal end of the catheter body. Two "puller" wires are anchored proximal each other, or one puller wire, and are manipulated to create curve in the intermediate section or tip section that deflects the esophagus. This is complex to manufacture and use. Manipulation of the wire (s) also will likely provide different levels of deflection when used by different practitioners, or by the same practitioner on a different occasion. The patent also discusses limiting the outer diameter of the catheter to about 8 French, which is about 2.6 mm A typical human esophagus has a relaxed diameter of about 2 cm. An 8 French deflection device will be easy to insert, but it will provide a small contact area with an esophagus wall during deflection. The force to achieve a deflection is concentrated in that area, and that concentrated force could create complications, after procedure discomfort, and could in an extreme case increase the likelihood of perforation.

Miller U.S. Pat. No. 7,621,908 discloses an esophageal catheter for displacing the catheter. The device includes a tube that extends through the esophagus past the diaphragm. The device is manipulated with control wires that are inserted through the tube in its lumen. The control wires have a curved portion that will displace the esophagus. The wires can be made of Nitinol and react to body temperature to have a curve when in the body. The wires can be manipulated by a practitioner to move the targeted area of an esophagus. Such manipulation can be inconsistent, and will also create relatively concentrated forces as discussed in the previous paragraph.

SUMMARY OF THE INVENTION

A preferred embodiment provides an esophageal deflection device. The device includes an elongate outer tube of biocompatible material having a proximal end and a distal end, the elongate outer tube being configured to contact walls of an esophagus, the elongate outer tube having a curved deflection between the distal end and the central portion, the elongate outer tube being flexible and resilient to maintain the curved deflection in a natural state and allow straightening of the elongate outer tube in response to force applied from within the elongate outer tube, the elongate outer tube being flexible enough to allow insertion and withdrawal from the esophagus, the curved deflection being stiffer than the esophagus such that the esophagus will conform to the shape of the curved deflection when the curved deflection is not straightened. The device also includes an elongate insertion tube or rod having a distal end and a proximal end, the elongate insertion tube being dimensioned to slide within the elongate outer tube, at least a portion of the elongate insertion tube being stiffer than the curved deflection of the elongate outer tube to create the force applied from within the elongate outer tube to at least partially straighten the curved deflection of the elongate outer tube when the portion of the elongate insertion tube is within the curved deflection of the elongate outer tube, the elongate insertion tube being sufficiently flexible to allow insertion into the esophagus while the portion of the elongate insertion tube is within the curved deflection of the elongate outer tube. The device preferably includes an elongate outer tube handle at the proximal end of the elongate outer tube forming a grip for a practitioner and an elongate insertion tube or rod handle at the proximal end of the elongate insertion tube or rod forming a grip for a practitioner. A length of the device is preferably predetermined to place the curved deflection at a targeted esophagus location near the left atrium of the heart. The curved deflection can be immediately adjacent the distal end of the elongate outer tube or separated by a straight portion of the elongate outer tube from the distal end of the elongate outer tube. The curved deflection can be U-shaped or is compound curve shaped. The elongate outer tube preferably includes bellows and the curved deflection includes bellows having different stiffness. A domed tip is preferably at the distal end of the elongate outer tube. The distal end of the elongate rod or tube can have a taper and the distal end and opening in the domed tip can be sized to permit a portion of the taper to extend through the opening the in the domed tip. The elongate outer tube and/or the insertion tube or rod can have a variable stiffness along. The device can include a depth insertion indicator and/or a radio opaque marker. The insertion tube or rod can have a lumen. Preferably, the outer diameter of the elongate outer tube is substantially matched to an esophagus inner diameter. Alternatively, an outer diameter of the elongate outer tube is at least half of an esophagus inner diameter. Alternatively, an outer diameter of the elongate outer tube is less than half of an esophagus inner diameter, the elongate outer tube further having suction ports for drawing a vacuum to draw esophagus walls into contact around the circumference of the elongate outer tube. Preferably, the device includes a plurality of temperature sensors disposed near an outermost surface of the elongate outer tube, which are preferably arranged in a three-dimensional pattern can be embedded in an outer coating of the elongate outer tube. The sensors are preferably arranged in orthogonal pairs along the device's longitudinal axis, exceeding the average length and area that the heart is in contact with the esophagus, and preferably increase in density in the region of curved deflection.

The invention also provides a method for conducting an esophageal deflection. The method includes inserting an insertion rod or tube into an elongate outer tube to straighten a curved deflection in the elongate outer tube. The method also includes inserting the elongate outer tube into an esophagus with the insertion rod to place the straightened curved deflection in a targeted region of the esophagus near the left atrium, and withdrawing the insertion rod or tube to allow the curved deflection to return to its natural shape and deflect the targeted region of the esophagus; wherein at least a portion of the elongate insertion tube is stiffer than the curved deflection of the elongate outer tube to create the force applied from within the elongate outer tube to at least partially straighten the curved deflection of the elongate outer tube The method can also include obtaining a three-dimensional heat map of the esophagus through a plurality of temperature sensors embedded near an outer surface of the elongate outer tube. The method can also include drawing a vacuum through a lumen in the insertion rod or tube.

The method can include introducing fluids or gas through a lumen in the insertion rod or tube. The method can include drawing a vacuum through suction ports in the elongate outer tube to draw esophagus walls onto the circumference of the elongate outer tube. Preferably, the outer diameter of the elongate outer tube is substantially matched to an esophagus inner diameter. Alternatively, an outer diameter of the elongate outer tube is at least half of an esophagus inner diameter. Alternatively, an outer diameter of the elongate outer tube is less than half of an esophagus inner diameter, and the method includes drawing a vacuum through suction ports to draw esophagus walls into contact around the circumference of the elongate outer tube.

BRIEF DESCRIPTION OF THE DRAWINGS

FIGS. 1A-1F illustrate a preferred esophageal deflection device of the invention;

FIGS. 2A-2D illustrate an experimental esophageal deflection device consistent with the FIGS. 1A-1F in insertion (straightened) and deflection states outside and within an esophagus;

FIGS. 3A-3C illustrate preferred domed tips for the elongate outer tube of the FIGS. 1A-1F esophageal deflection device;

FIGS. 4A-4C illustrate preferred variable stiffness sections in a curved deflection region of the elongate outer tube of the esophageal deflection device;

FIGS. 6A-6E illustrate temperature sensors in a preferred esophageal deflection device of the invention, an example finite element analysis of esophagus temperature during an ablation procedure, and experimental temperature versus time data from ex vivo testing of porcine esophagus and heart.

DETAILED DESCRIPTION OF THE PREFERRED EMBODIMENTS

A preferred embodiment of the invention is an esophageal deflection device. The device includes a resilient outer elongate tube with a naturally curved section dimensioned and configured to insert into an esophagus and deflect the esophagus and another retractable tube or rod for reducing the curved section during insertion into the esophagus and allowing the naturally curved section of the elongate outer tube to return resiliently to its natural shape under control of a practitioner during a procedure to deflect the esophagus. In preferred embodiments, an insertion tube or rod slides within the outer elongate tube. The insertion tube or rod has portion that is stiffer than the elongate other tube.

The device can include additional features, such as a temperature probe, pressure/force sensor, or x-ray detectable insert desired at contact edge or along tube for feedback to user. By using a radio opaque material at the tip, cardiologists can use tools most familiar to them to identify location of indicators where the highest probability of insertion depth is necessary for specific classes of persons. This can correlate to body height, for example. Additional sensors can be used before and during a thermal ablation procedure. Temperature and flex sensor positions can be optimized for quality readings for state of esophagus in real time Preferred devices are simple to use, even for less experienced practitioners. A device of the invention can reduce surgeon fatigue and reduce overall operation time for procedures that require or benefit from a deflection of the esophagus. The curve is created by a simple retraction of the retractable element, which allows the curved section to return to its natural curved shape and deflect the esophagus. A simply sliding movement can be monitored precisely via markings. The naturally curved section has a predetermined shape that will not diverge from the intended design shape during a procedure. The exact predetermined natural curve is replicated during use of the device in a procedure, and therefore the amount of curve will not exceed or be less than that defined by the predetermined shape.

Preferred embodiments of the invention will now be discussed with respect to experiments and drawings. Broader aspects of the invention will be understood by artisans in view of the general knowledge in the art and the description of the experiments that follows.

Figure 1C:
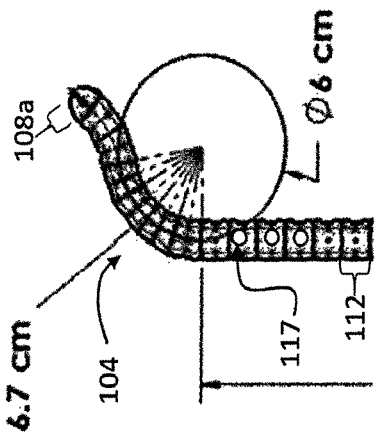
Figure 1B:
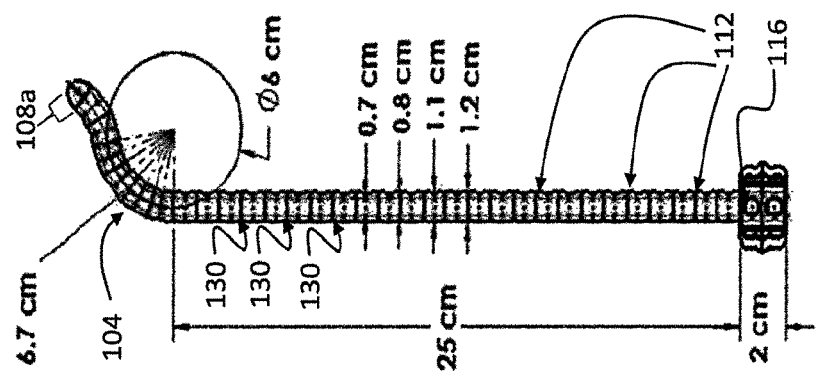
Figure 1A:
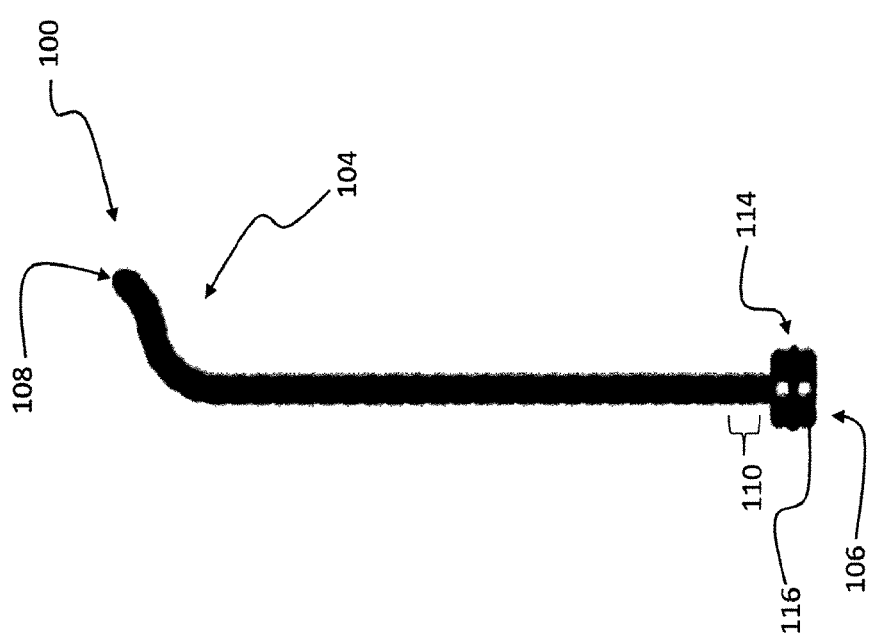

FIGS. 1A-2B show a preferred esophageal deflection device of the invention. FIGS. 1A-1C illustrate an outer tube 100 and FIGS. 1D-1F illustrates an insertion tube or rod 102 that slides into a lumen of the outer tube 100 to straighten a curved deflection 104. FIGS. 2A and 2B respectively illustrate an insertion state of the deflection device and a deflection state of the deflection device.

The elongate outer tube 100 is made of biocompatible material having a proximal end 106 and a distal end 108. An outside diameter of the elongate outer tube 100 is preferably substantially matched to an esophagus inner diameter, e.g. approximately equal to the inner diameter or 80-90-% of the inner diameter. A length from a central portion 110 to the distal end 108 is selected to place the curved deflection 104 at a targeted area of the esophagus adjacent the left atrium. The elongate outer tube 100 includes the curved deflection 104 between the distal end 108 and the central portion 110. In FIG. 1A, the curved deflection 104 is immediately adjacent the distal end 108 and is a compound deflection, having two different curves, but the curved deflection 104 can also be separated from the distal end 108, and closer to the central portion, such as when a U-shaped curved deflection is used. The elongate outer tube 100 is flexible to allow insertion into and withdrawal from an esophagus without injury, but resilient to maintain the curved deflection 104 in a natural state (when the insertion tube or rod 102 is not within a lumen of the curved deflection 104) and allow straightening of the curved deflection 104 in response to force applied from within the elongate outer tube 100 when the insertion tube or rod is within the curved deflection 104). At least the curved deflection 104 is stiffer than the esophagus such that the esophagus will conform to the shape of the curved deflection 104. The elongate outer tube 100 preferably consists of many equal length bellow segments 112 that extend from an elongate outer tube handle 114 at the distal end of the elongate outer tube forming a grip for a practitioner. The handle 114 includes one or more (two are shown) viewing holes 116 through which a practitioner can observe markings on the insertion tube or rod 102. The distal end 108 preferably includes a domed tip 108a, that provides a gradual increase of device diameter to allow for a decreased stiffness at the tip, which could alternatively be provided by having different material properties at the tip. FIGS. 1B and 1C. The FIGS. 1B and 1C illustrate example dimensions for a preferred embodiment deflection device. In FIGS. 1B and 1C, the dimensions were of the experimental device that correlated to pig esophagi and hearts that were used to test the prototype. The dimensions can be selected so that the outer diameter of the elongate outer tube substantially matches, as discussed above or alternatively is at least half the inner esophagus diameter. Smaller diameters can also be used, e.g., 3-20 mm, if the elongate outer tube includes suction ports 117 (see FIG. 1C, which shows a few suction ports, which could be disposed through the length of the elongate outer tube or only be in the region of the curved deflection). Suction ports 117 permit pulling a vacuum to draw walls of the esophagus against the elongate outer tube 100 around its entire circumference. Preferably, the diameter and/or vacuum insures contact between all outermost diameter surfaces of the elongate outer tube 100 and the esophagus. This will vary for classes of patients, however, such as being different for age groups and size groups. Length also is selected to allow a practitioner to comfortably grasp the handle 114 at a distance away from a patient mouth while positioning the curved deflection 104 at the targeted portion of the esophagus near the left atrium. An example length is about 40 cm. A typical adult human has an esophagus of about 20-25 cm, and the additional 15 cm provides a comfortable position to grip the handle away from a patient mouth. The esophagus lengthens from birth through adulthood, and the length can be set by age. There are also variances with gender and other physical characteristics. Published information can provide guidance on typical lengths and diameters. See, e.g., Song et al., "Correlation of Esophageal Lengths with Measurable External Parameters," Korean J Internal Medicine, January 1991 6(1).

The elongate outer tube 100 in experiments was formed of a thermoplastic elastomer molded over with a silicone. Other suitable coatings include rubber or similarly compliant material. Other polymers, and mixtures of polymers could be used for optimal and varying stiffness properties including nylon, polyurethane, or polyethylene, etc. The elongate outer tube 100 is preferably a unitary, single piece design. An experimental device for demonstrating the deflection ability in in vivo testing did not use biocompatible materials and was 3D printed. The experimental materials were a mixture of TangoBlackPlus and VeroClear (which are two photopolymers) and the elongate outer tube was made using a Stratasys Objet 350 Connex3. The 3D printing allowed easy mixing of materials with different stiffness. Other experimental devices for in vivo tests were tested with a longer esophagus with a deviated shape, and the elongate outer tube was formed from a thermoplastic tubing that was thermoformed to that deviated shape.

A biomedical grade tubing can be thermoformed with the specified radius of curvature for either the U or L shape designs of the deflection curve of the elongate outer tube 100, including with bellows that are preferred to reduce the risk of kinking. Then, a silicone rubber or other compliant material can be casted onto the tubing mold. Stiffness can change longitudinally along the device to promote curvature at inflection points. This can be achieved through material mixing/layering or through alterations in geometry including changing of inner and outer diameter or material removal (i.e. precisely placed holes). Other forms of manufacturing include injection molding and material additive processes such as 3D printing. Such additive processes can produce varying material designs by layering altering mixtures of materials or by changing geometry. 3D printing can be used to customize devices before procedures where specific geometric or material mixing changes are needed, i.e., a person with irregular anatomy due to age, weight, or other, to vary the location or amount of deflection relative to the heart or other anatomical markers.

With reference to FIGS. 1D-1F, the elongate insertion tube or rod 102 has a distal end 118 and a proximal end 120. The elongate insertion tube is dimensioned to slide within the elongate outer tube 100, and at least a portion 122 of the elongate insertion tube or rod 102 is stiffer than the curved deflection 104 of the elongate outer tube 100 to create the force applied from within the elongate outer tube 100 to at least partially straighten the curved deflection 104 of the elongate outer tube when the portion 122 of the elongate insertion tube or rod 102 is within the curved deflection 104 of the elongate outer tube. The elongate insertion tube or rod 102 is sufficiently flexible to allow insertion into the esophagus while the portion of the elongate insertion tube or rod 102 is within the curved deflection 104 of the elongate outer tube 100.

The insertion tube or rod 102 in experiments was formed of non-biocompatible materials discussed above with respect to the elongate outer tube. It is preferably a unitary single pieced design. The insertion tube or rod provides more rigidity to the deflection device. It both strengthens the device and prevents buckling/kinking. It can have a flexible, tapered, and/or dome tip with a hole extended by a lumen from the proximal to distal end. The tip can extend beyond the elongate outer tube 100 through a hole 108b (see FIGS. 3A-3B) to help guide the deflection device down the esophagus. The insertion tube or rod 102 can have stiffer sections near the regions that straighten the curved deflection 104.

FIG. 1E illustrates exemplary dimensions for the insertion tube or rod 102 that was used for the experiments on porcine esophagi and hearts. In the example devices, a typical distance from the handle 126 to the distal end is 34 cm, the outer diameter is 7 mm cm at a central portion and can taper to the distal tip 118. A length of the handle 126 is 4 cm. The dimensions would be adjusted per guidance above and relative to the outer elongate tube 100. The insertion tube or rod 102 includes a handle 126 (FIG. 1E), and that handle is preferably a comfortable distance away from the handle 114 when the insertion tube or rod 102 is fully inserted (FIG. 2A). The handles 114 and 126 can be separated by a few centimeters, or 5-20 cm, for example. As discussed above, the dimensions can vary depending upon the class of patient being treated FIG. 1F shows the distal tip 122, which can have variable stiffness. Having variable stiffness sections 122a and 122b (disposed longitudinally to provide various stiffness in the longitudinal direction) in the distal tip 122 can provide balance between the curved deflection 104 and the straightening of the curved deflection 104 by the insertion tube. This is further constrained by minimum pressure needed to deflect the esophagus and maximum pressure the esophagus is capable of handling. Having programmable stiffness longitudinally along both the overtube and the insertion piece is very valuable and allows geometry in general (diameter, ID vs OD, radius of curvature, etc.) to not be the only form of changing flexibility/rigidity on a device.

Referring to FIG. 1E, markings 124 are preferably included on an outer surface of the elongate insertion tube or rod 102, and the markings 124 can be viewed through the viewing holes 116 of the handle 114 of the elongate outer tube. The markings 124 are separated from a 126 handle at the distal end 120 of the elongate insertion tube or rod 102, which handle 126 forms a grip for a practitioner. The markings 124 and the viewing holes together provide a depth insertion indicator, which indicates the relative position of the elongate insertion tube or rod 102 in the outer tube 100.

Radio opaque markers are preferably including on the elongate outer tube 100 and can also be placed on the insertion tube or rod 102. The markers can be in the region of the curved deflection 104 to assist in positioning the curved deflection 104 near the left atrium of the heart for deflection away from the heart when the insertion tube or rod 102 is within and straightening the curved deflection. The markers are placed to allow the device and its shape within the esophagus to be visible under X-ray (conveniently, cardiac ablation procedures already utilize X-ray imaging so the use of the deflection device does not add an X-ray imaging step). The markers may within a coating of the outer tube 100, for example placed at bellows in the curved deflection section 104 or throughout the length of the elongate outer tube 100. FIGS. 1B and 1E respectively show bands 130 of opaque material (e.g. polymer bands, coatings, etc.) located at each bellow, a few of which are labelled with the reference numeral 130, and a band at the most proximal portion of the distal tip 122. Placement on the insertion tube or rod 102 can help place the position of the insertion tube or rod relative to the curved deflection, and can aid small manipulations and re-positioning. Another option is to place opaque material with temperature sensor pairs, as discussed below with respect to FIGS. 6A and 6B. Placing opaque markers near temperature sensors is preferred to minimize the distance between the ablation site (also radiopaque) and the locations where the temperature is being sensed.

Figure 2C:
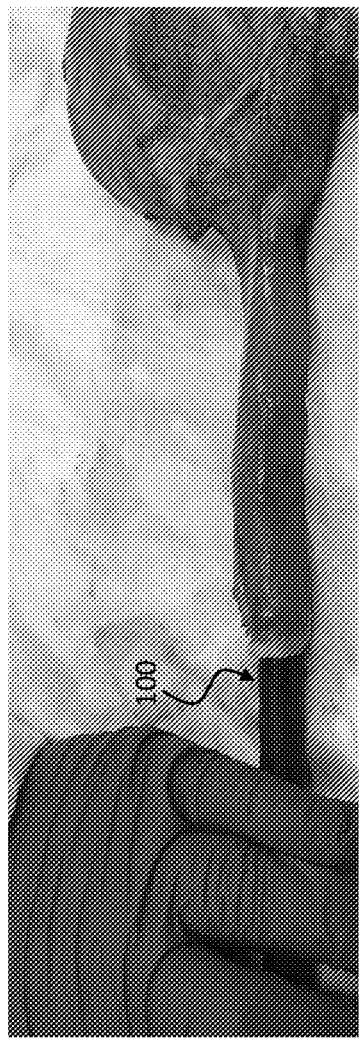
Figure 2D:
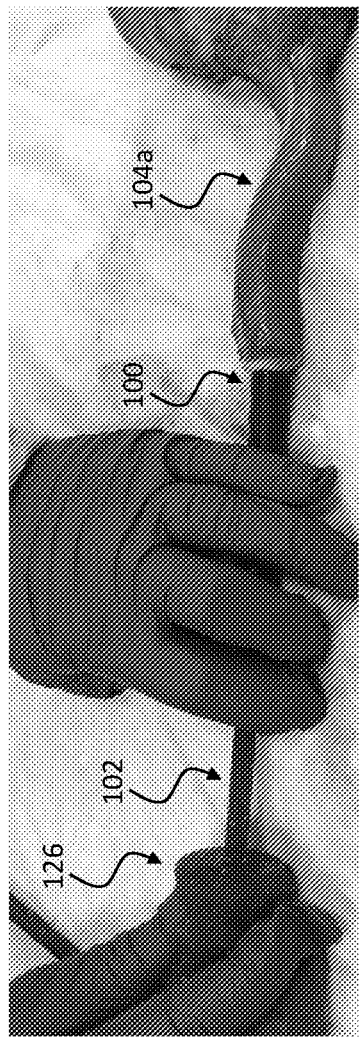

FIGS. 2A and 2B illustrate respective straightened and deflection states of an experimental embodiment consistent with FIGS. 1A-1F. The straightened state of FIG. 2A is the state in which the deflection device would be inserted into an esophagus and withdrawn from an esophagus. The deflection state of FIG. 2B is achieved by withdrawal of the insertion tube or rod 102 by gripping the handles 126 and 114 and withdrawing the handle 126 proximally. When the insertion tube or rod is moved a sufficient distance, its distal tip 122 is withdrawn from the curved deflection 104 and the curved deflection 104 resiliently returns to its natural position shown in FIG. 1B and the targeted esophagus portion takes on the shape of the curved deflection. FIGS. 2C and 2D respectively illustrate the insertion/straightened state and the deflected state from an in vitro experiment with a porcine esophagus and heart. A targeted portion of the esophagus 104a is forced to take on the shape of the curved deflection 104 when the distal tip 122 of the insertion tube or rod 102 is withdrawn from the curved deflection. Experiments demonstrated the invention in vitro. A simple procedure inserts the device and a controlled deflection of the esophagus is easily achieved and reversed. The insertion can be to a precise predetermined depth. Withdrawal of the device is safe and simple. Once the insertion tube or rod 102 is slid out, the curved deflection 104 of the flexible elongate outer tube 100 has proper (multi-inflectioned U or L like shape) geometry, rigidity and torsional stiffness to force the targeted portion of the esophagus into the shape of the curved deflection. The curved deflection can have a back bone (or another material) or can consist itself of material to ensure torsional stiffness so that the elongate outer tube 100 of the device can be simply rotated by hand or robotic interface to manipulate the position of the curved deflection 104 and move the esophagus away from the left atrium of the heart. Rotation can be useful to ensure deployment would be properly oriented to deflect away from the heart, or after deployment to manipulate further Although torsionally stiff, the structure of the curved deflection 104 should be flexible transversely and can vary in stiffness in the longitudinal direction.

FIGS. 3A-3C illustrate some variations for the domed tip 108a of the elongate outer tube. In FIG. 3A, a hole 108b in the domed tip is large diameter, such as large as the inner diameter of the elongate outer tube 100, in which case the distal tip 122 would push through the hole 108b and guide insertion. The hole 108b in FIG. 3B is smaller, which can as small as 1 mm, for example. FIG. 3C shows an elongate "Maloney" style tapered tip 108a with a hole 108b sized as in FIG. 3B. The hole 108b can also be sized smaller than the inner diameter of the elongate outer tube 100, but still large enough to allow, for example, a portion of the tapered distal tip to extend through the hole, as discussed above. The insertion tube or rod 102 might also include or consist of an endoscope that can provide visual assistance in insertion of the deflection device. The insertion tube or rod 102 can include a lumen as a working channel to deliver air/fluid to the distal end 118 and or pull a vacuum to bring the esophagus in fuller contact with the outer surface of the elongate outer tube 100.

Figures 5A, 5B, 5C:
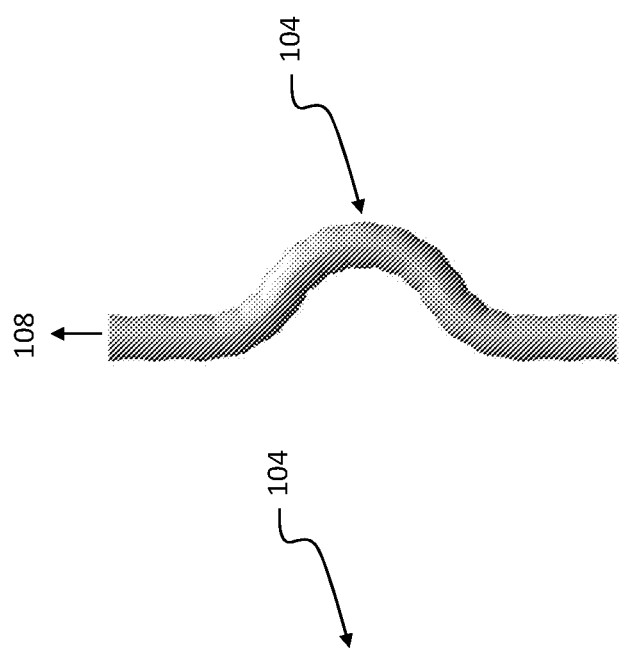
FIGS. 5A-5C illustrate preferred U-shaped curved deflections for elongate outer tube of the esophageal deflection device.

FIGS. 4A-4C illustrate a preferred strategy for achieving different shapes of the curved deflection 104 of the elongate outer tube 100. In FIGS. 4A-4C, the majority of the outer tube 100 includes bellow segments 112a of a first stiffness. A predetermined and tailored deflection curve 104 is produced in an area where bellow sections 112b are included. FIG. 3B includes additional sections 112c of a third stiffness, and FIG. 3C a section 112d of a fourth stiffness. A strategy for providing the curved deflection includes least stiff to most stiff sections: 112a, 112b, 112c, where the most stiff is 112d. As discussed above, the variable stiffness can be formed by process including alteration of material properties, wall thickness, adding holes, etc. The elongate outer tube 100 in the curved deflection section 104 of FIGS. 4A-4C has varying stiffness, typically more stiff around the inflection points and a very flexible leading edge of the domed tip 108a if fully extended for insertion. The outer part of the elongate outer tube should be smooth and compliant/soft to prevent perforations. FIGS. 5A-5C illustrate that the curved deflection 104 can be tailored to have a different shape, particularly different "U-shaped" deflections, and that the curved deflection 104 can be proximally separated from the distal end 108 of the elongate outer tube.

Figure 6A:
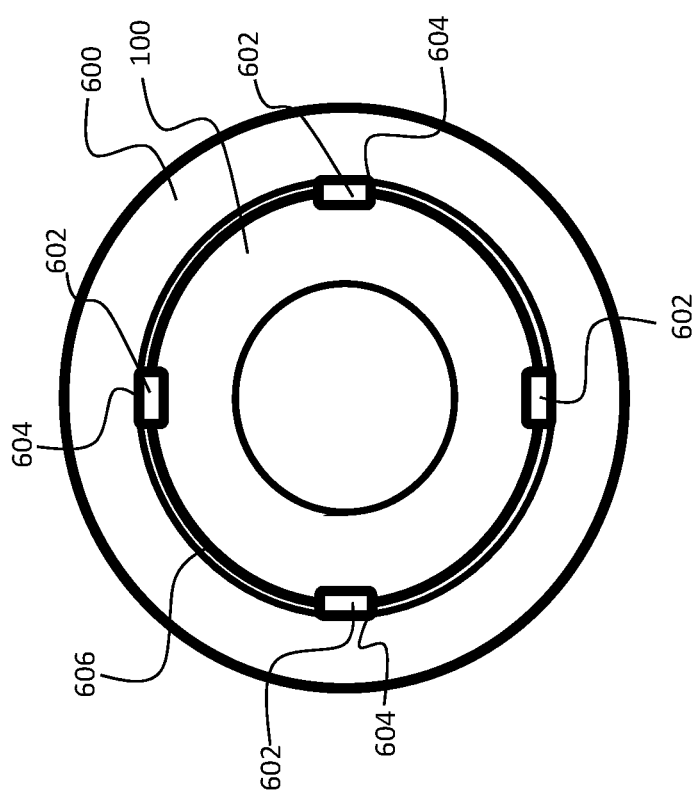
Figure 6D:
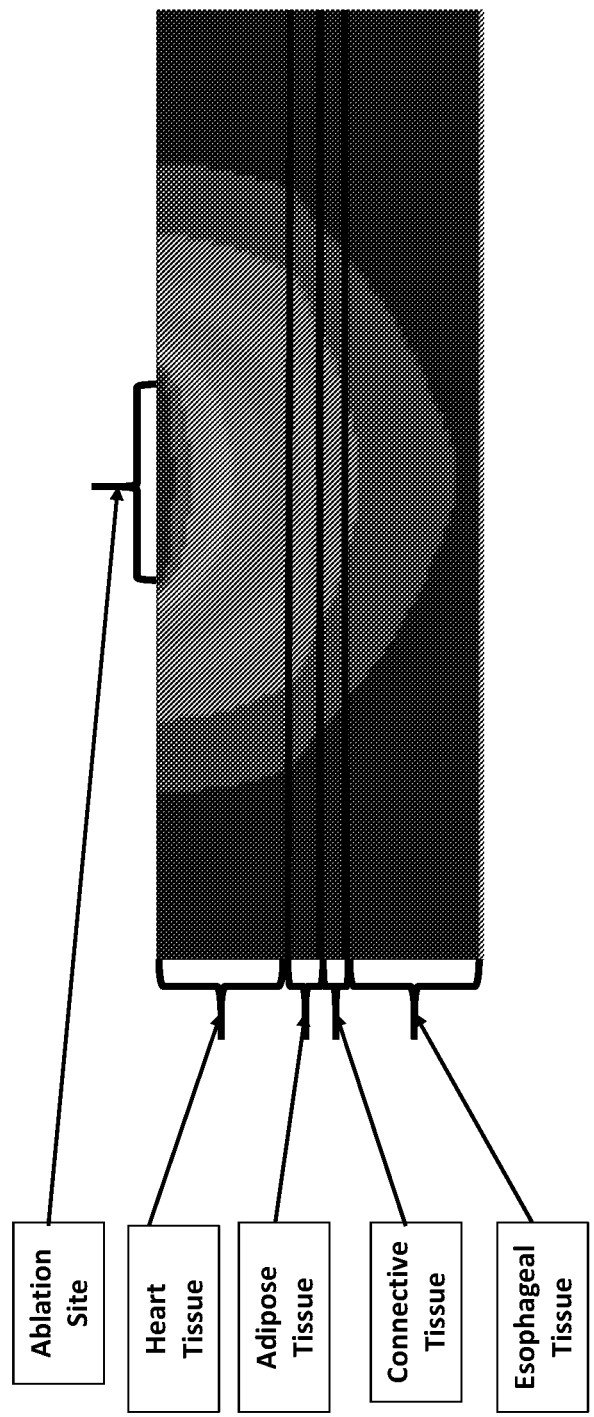
Figure 6E:
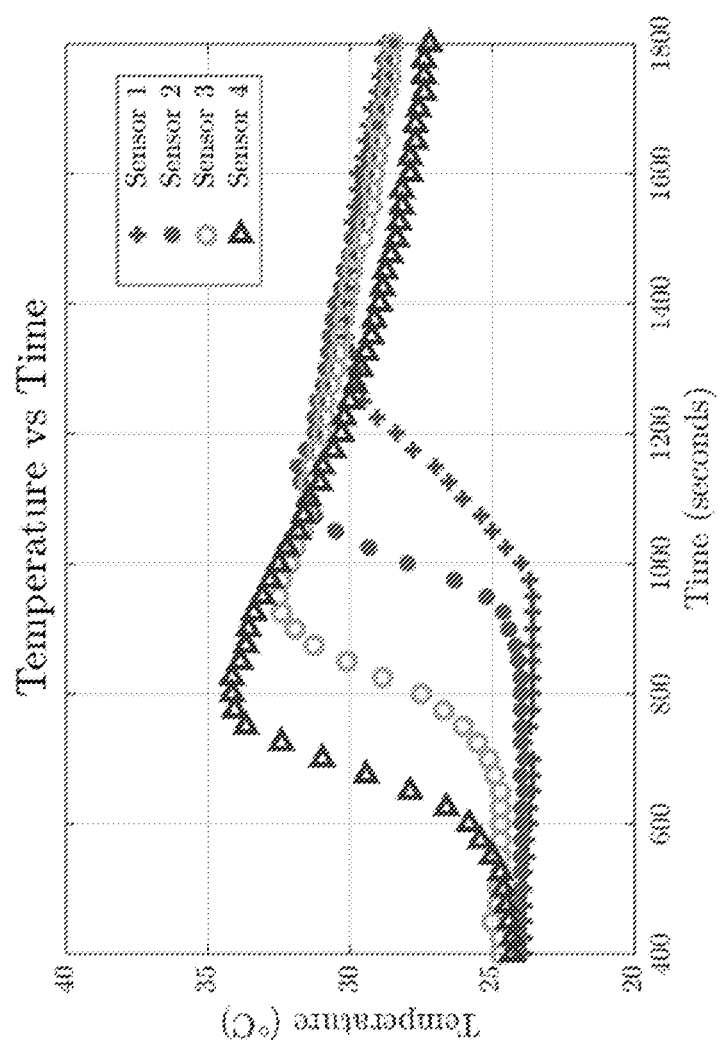

FIGS. 6A-6D illustrates a preferred variation to include temperature sensing in the deflection device. FIG. 6A shows a cross-section of the deflection device inserted in an esophagus 600. Unlike prior devices, the present invention can accurately measure esophagus temperature during a deflected state and during an ablation procedure. Thermister (preferably negative temperature coefficient (NTC)) or other suitable temperature sensors 602 are embedded in the outer tube 100. The sensors are covered with a conductive material 604 and are embedded/covered by an outer layer 606 such as silicone of the elongate outer tube 100. The sensors 602 senses and monitors the luminal temperature of the esophagus after insertion. As shown in FIG. 6B, which shows the elongate outer tube and temperature sensors before the sensors are covered with the outer layer 606, indicates that preferably the density (number per longitudinal length or surface area of the elongate outer tube 100) increases towards the distal end 108 to increase the ability of the device to sense temperature near the ablation site. The sensors 602 form a three-dimensional arrangement and can be situated near the outer surface of tube 100 covered by a thin amount of the outer layer 606 (see FIG. 6C, which is a portion of FIG. 6B after the outer layer 606 has been coated onto the elongate outer tube 100) to enable the luminal tissue surface temperature to always be sensed both radially and longitudinally. Preferably, the sensors 602 are situated in orthogonal pairs along the device's longitudinal axis, exceeding the average length and area that the heart is in contact with the esophagus. The sensors can provide signals via a layer of conductive material 604 that spans and covers the area in which the temperature sensors are placed. In experiments, wiring to connect sensors and return signals was embedded in the silicon outer layer 606. The wires must be arranged to avoid interference with bending and to avoid breaking during bending, and relaxation in the wires or a wiring harness along the length of the elongate outer tube can avoid such problems. Any strategy to provide a reliable signal path and maintain contact with the temperature sensors 602 can be used. The arrangement can ensure that the sensors 602 will detect any substantial temperature increase on the surface of the esophagus, which would indicate that ablation should be paused. The arrangement allows mapping on the computational side to take place paired with complementary analytical models to suggest where heat source is coming from. This was also tested experimentally and an example finite element analysis is shown in FIG. 6D, indicating the temperature distribution in four tissue layers from an ablation catheter (at the ablation site) to the esophagus. The model describes the esophageal wall, connective tissue, adipose tissue, and heart tissue and has been developed to simulate the temperature profile extending from a heat source similar to that of an rf ablation tool. The simulated temperature profile of FIG. 6D includes thermal conductivity parameters consistent with the associated materials for each layer. Such thermal mapping can provide a worst-case scenario by continuously mapping a similar profile with the discrete temperature values and locations in a 3-dimensional arrangement. Currently, when temperature rises only a small amount (e.g., 1 degree Celsius over body temperature), a surgeon may feel required to manipulate the esophagus or pause the procedure. The preferred deflection device with the ability to provide a 3D map of temperature can provide valuable detailed information leading to a more informed decision on whether or not to proceed with the surgery, or to rotate the deflection device to change the position of the esophagus. In experiments, temperature data has been collected from ex vivo experimental tests using a pig esophagus and heart layered in a similar manner as the model simulated in FIG. 6D. Recorded data in FIG. 6E show the rise in temperature as seen from the esophageal wall while the heat source is introduced and held to a point on the inner left atrium heart lining Sensors are preferably placed relative to one another to be capable of accurately predicting significant temperature rises between each other. This is to account for the case of an ablation catheter pressed at a location between sets of orthogonally paired sensor.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An esophageal deflection device, the device comprising:
an elongate outer tube of biocompatible material comprising a proximal end and a distal end and a central portion therebetween, wherein the elongate outer tube is capable of being flexed if a threshold amount of force is applied, the elongate outer tube comprising a curved deflection between the distal end and the central portion; the curved deflection comprising a stiffness sufficient to cause the esophagus to conform to the shape of the curved deflection when the elongate outer tube is inserted into the esophagus;

an elongate insertion tube or rod comprising a distal end and a proximal end, the elongate insertion tube being smaller in diameter than the elongate outer tube, the elongate insertion tube being formed of material comprising a stiffness sufficient to create the threshold amount of force applied from within the elongate outer tube to at least partially straighten the curved deflection when the elongate insertion tube or rod is inserted in the deflection, wherein a length of the elongate outer tube from a central portion to the distal end is predetermined to place the curved deflection at a targeted esophagus location near the left atrium of the heart and the curved deflection is U-shaped or is compound curve shaped; and a handle at the proximal end of the elongated outer tube, the handle comprising view holes to view markings on the elongate insertion tube or rod, the markings and view holes combining to provide a depth insertion indicator, which indicates the relative position of the elongate insertion tube or rod in the elongate outer tube, wherein the elongate outer tube comprises bellows and the curved deflection includes bellows comprising different stiffnesses, wherein the bellows comprising different stiffnesses in the curved deflection comprise a section of one or more bellows of lesser stiffness between two sections of one or more bellows of a greater stiffness.

2. The device of claim 1, wherein the curved deflection is immediately adjacent the distal end of the elongate outer tube and the curved deflection is separated by a straight portion of the elongate outer tube from the distal end of the elongate outer tube.

3. The device of claim 1, comprising a domed tip at the distal end of the elongate outer tube with an opening in the domed tip.

4. The device of claim 3, wherein the distal end of the elongate insertion rod or tube comprises a taper and the distal end and opening in the domed tip are sized to permit a portion of the taper to extend through the opening the in the domed tip.

5. The device of claim 1, wherein the elongate insertion tube comprises a variable stiffness along a length of the elongate insertion tube.

6. The device of claim 1, comprising one or all of the depth insertion indicator, radio opaque marker, and a lumen in the insertion tube or rod.

7. The device of claim 1, wherein the insertion tube or rod comprises or consists of an endoscope.

8. The device of claim 1, wherein an outer diameter of the elongate outer tube is substantially matched to an esophagus inner diameter.

9. The device of claim 1, wherein an outer diameter of the elongate outer tube is at least half of an esophagus inner diameter.

10. The device of claim 1, wherein an outer diameter of the elongate outer tube is less than half of an esophagus inner diameter, the elongate outer tube further comprising suction ports for drawing a vacuum to draw esophagus walls into contact around a circumference of the elongate outer tube.

11. The device of claim 1, comprising a three-dimensional arrangement of plurality of temperature sensors disposed near an outermost surface of the elongate outer tube.

12. The device of claim 11, wherein the elongate outer tube comprises an outer coating and the temperature sensors are embedded in the coating.

13. The device of claim 11, wherein the temperature sensors are arranged at the curved deflection in orthogonal pairs along a longitudinal axis of the elongate outer tube in an arrangement to provide a 3D map of temperature, wherein ones of the orthogonal pairs are proximal from the curved deflection and other ones of the orthogonal pairs are distal from the curved deflection.

14. The device of claim 11, wherein the temperature sensors are arranged in orthogonal pairs along a longitudinal axis of the elongate outer tube including the central portion and increase in density in a region of the curved deflection compared to temperature sensors arranged in other portions of the elongate outer tube.

* * * * *